US010626142B2

(12) United States Patent
Tustian et al.

(10) Patent No.: US 10,626,142 B2
(45) Date of Patent: Apr. 21, 2020

(54) PURIFICATION PLATFORM FOR BISPECIFIC ANTIBODIES

(71) Applicant: REGENERON PHARMACEUTICALS, INC., Tarrytown, NY (US)

(72) Inventors: Andrew Tustian, Tarrytown, NY (US); Christine Endicott, Glastonbury, CT (US); Benjamin Adams, Mount Vernon, NY (US); John Mattila, Nyack, NY (US); Hanne Bak, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 493 days.

(21) Appl. No.: 14/808,171

(22) Filed: Jul. 24, 2015

(65) Prior Publication Data

US 2016/0024147 A1   Jan. 28, 2016

Related U.S. Application Data

(60) Provisional application No. 62/029,463, filed on Jul. 26, 2014.

(51) Int. Cl.
| | | |
|---|---|---|
| *C07K 1/22* | (2006.01) | |
| *C07K 16/06* | (2006.01) | |
| *B01J 39/08* | (2017.01) | |
| *B01J 39/26* | (2006.01) | |
| *B01D 15/38* | (2006.01) | |

(52) U.S. Cl.
CPC ............ *C07K 1/22* (2013.01); *B01D 15/3819* (2013.01); *B01D 15/3828* (2013.01); *B01J 39/08* (2013.01); *B01J 39/26* (2013.01); *C07K 16/065* (2013.01); *C07K 2317/14* (2013.01); *C07K 2317/31* (2013.01); *C07K 2317/526* (2013.01)

(58) Field of Classification Search
None
See application file for complete search history.

(56) References Cited

U.S. PATENT DOCUMENTS

| | | |
|---|---|---|
| 5,807,706 A | 9/1998 | Carter et al. |
| 5,945,311 A | 8/1999 | Lindhofer et al. |
| 5,985,276 A | 11/1999 | Lindhofer et al. |
| 6,165,745 A | 12/2000 | Ward et al. |
| 6,551,592 B2 | 4/2003 | Lindhofer et al. |
| 6,994,853 B1 | 2/2006 | Lindhofer et al. |
| 7,018,632 B2 | 3/2006 | Lindhofer et al. |
| 7,169,903 B2 | 1/2007 | Schuman et al. |
| 7,262,028 B2 | 8/2007 | Hendrikus et al. |
| 7,820,799 B2 | 10/2010 | Godavarti |
| 8,062,640 B2 | 11/2011 | Sleeman et al. |
| 8,586,713 B2 | 11/2013 | Davis et al. |
| 2002/0051780 A1 | 5/2002 | Lindhofer et al. |
| 2002/0062010 A1 | 5/2002 | Arathoon et al. |
| 2003/0224000 A1 | 12/2003 | Kokai-Kun et al. |
| 2007/0148165 A1 | 6/2007 | Shitara et al. |
| 2007/0196363 A1 | 8/2007 | Arathoon et al. |
| 2014/0112914 A1 | 4/2014 | Nezu et al. |
| 2015/0239991 A1* | 8/2015 | Blein ................. B01D 15/3809 530/389.5 |

FOREIGN PATENT DOCUMENTS

| | | | | |
|---|---|---|---|---|
| EP | 2522724 A1 * | 11/2012 | ............... | C07K 1/22 |
| GB | 2197322 A | 5/1988 | | |
| GB | 2197323 A | 5/1988 | | |
| WO | 2008121865 A1 | 10/2008 | | |
| WO | WO-2010030222 A1 * | 3/2010 | ........... | B01D 15/363 |
| WO | 2010151792 A1 | 12/2010 | | |
| WO | 2012123520 A1 | 9/2012 | | |
| WO | 2013136186 A2 | 9/2013 | | |
| WO | 2014049003 A1 | 4/2014 | | |
| WO | 16/018740 A2 | 2/2016 | | |

OTHER PUBLICATIONS

Johann Deisenhorfer, "Crystallographic Refinement and Atomic Models of a Human Fc Fragment and Its Complex with Fragment B of Protein A from *Staphylococcus aureus* at 2.9- and 2.8-A Resolution", Biochemistry, vol. 20, No. 9, Apr. 28, 1981, pp. 2361-2370.

Duhamel, et al., "pH Gradient Elution of Human IgG1, IgG2 and IgG4 from Protein A-Sepharose", Journal of Immunological Methods, vol. 31, 1979, pp. 211-217.

Jendeberg, et al., "Engineering of $Fc_1$ and $Fc_3$ from human immunoglobulin G to analyse subclass specificity for staphylococcal protein A", Journal of Immunological Methods, vol. 201, 1997, pp. 25-34.

Lindhofer, et al., "Preferential Species-Restricted Heavy/Light Chain Pairing in Rat/Mouse Quadromas: Implications for a Single-Step Purification of Bispecific Antibodies", The Journal of Immunology, 155(1), 1995, pp. 219-225.

(Continued)

*Primary Examiner* — Daniel E Kolker
*Assistant Examiner* — James L Rogers
(74) *Attorney, Agent, or Firm* — Schwabe, Williamson & Wyatt PC; Kristan Lansbery (57) ABSTRACT

High resolution protein A chromatography employing a chaotropic agent and pH gradient or pH step elution buffer results in improved peak resolution between closely related molecular species. Bispecific antibodies containing a protein A-binding-ablating substitution CH3 domain paired with a protein A-binding CH3 domain are separated with high peak resolution from monospecific antibodies containing a protein A-binding-ablating substituted CH3 domain paired with the protein A-binding-ablating substituted CH3 domain and monospecific antibodies containing a protein A-binding CH3 domain paired with the protein A-binding CH3 domain. Useful chaotropic agents include magnesium chloride and calcium chloride.

40 Claims, 4 Drawing Sheets

(56) References Cited

OTHER PUBLICATIONS

Lindmark, et al., "Binding of Immunoglobulins to Protein A and Immunoglobulin Levels in Mammalian Sera", Journal of Immunological Methods, vol. 62, 1983, pp. 1-13.
Linhult, et al., "Improving the Tolerance of a Protein A Analogue to Repeated Alkaline Exposures Using a Bypass Mutagenesis Approach", Proteins: Structure, Function, and Bioinformatics, vol. 55, 2004, pp. 407-416.
Nagaoka, et al., "Single amino acid substitution in the mouse IgG1 Fc region induces drastic enhancement of the affinity to protein A", Protein Engineering, vol. 16, No. 4, 2003, pp. 243-245.
Nilsson, et al., "A synthetic IgG-binding domain based on staphylococcal protein A", Protein Engineering, vol. 1, No. 2, 1987, pp. 107-113.
Ridgway, et al., "'Knobs-into-holes' engineering of antibody $C_H3$ domains for heavy chain heterodimerization", Protein Engineering, vol. 9, No. 7, 1996, pp. 617-621.
Sasso, et al., "Human IgM Molecules That Bind Staphylococcal Protein A Contain $V_H$III H Chains", The Journal of Immunology, vol. 142, No. 8, Apr. 15, 1989, pp. 2778-2783.
Sasso, et al., "Human IgA and IgG F(ab'), That Bind to Staphylococcal Protein A Belong to the $V_H$III Group", The Journal of Immunology, vol. 147, No. 6, Sep. 15, 1991, pp. 1877-1883.
Schroeder, et al., "Structure and evolution of mammalian $V_H$ families", International Immunology, vol. 2, No. 1, 1990, pp. 41-50.
Seldon, et al., "Improved Protein-A separation of $V_H3$ Fab from Fc after Papain Digestion of Antibodies", Journal of Biomolecular Techniques, vol. 22, 2011, pp. 50-52.
Starovasnik, et al., "Antibody variable region binding by Staphylococcal protein A: thermodynamic analysis and location of the Fv binding site on E-domain", Protein Science, vol. 8, 1999, pp. 1423-1431.
Third party observations filed on Aug. 9, 2012 by MacLean, Martin R. in European Patent Application No. 10726775.9.
Van Loghem, et al., "Staphylococcal Protein A and Human IgG Subclasses and Allotypes", Scand. J. Immunol., vol. 15, 1982, pp. 275-278.
Walter, et al., "Analysis of Genetic Variation Reveals Human Immunoglobulin VH-Region Gene Organization", American Journal Human Genetics, vol. 42, 1988, pp. 446-451.
Fernandez-Rodriguez, Jesus, "Induced heterodimerization and purification of two target proteins by a synthetic coiled-coil tag," Protein Science, vol. 21, No. 4, Feb. 23, 2012, pp. 511-519.
U.S. Appl. No. 62/029,463, filed Jul. 26, 2014, Expired.
PCT/US2015/041936, Jul. 24, 2015, WO 2016/018740, Expired.
Ghose et al., "Antibody Variable Region Interactions with Protein A: Implications for the Development of Generic Purification Processes," Wiley InterScience, vol. 92 (No. 6):665-673, Dec. 20, 2005.
Tustian et al., "Development of a Novel Affinity Chromatography Resin for Platform Purification of Bispecific Antibodies with Modified Protein A Binding Avidity," Biotechnol. Prog., vol. 34 (No. 3):650-658, (2018); DOI: 10.1002/btpr.2622.

* cited by examiner

PURIFICATION PLATFORM FOR BISPECIFIC ANTIBODIES

FIELD

A method for purifying a specific multimeric protein from a complex mixture of proteins via affinity chromatography is provided. Specifically a method for isolating a heterodimer (including bispecific antibody) from a complex mixture of monomers and homodimers via affinity chromatography (including protein A chromatography) using a chaotropic agent is provided.

BACKGROUND

Multiple bispecific antibody formats have been proposed and are currently under development. One such format is based upon a standard fully human IgG antibody having an improved pharmacokinetic profile and minimal immunogenicity (see U.S. Pat. No. 8,586,713, which is incorporated herein in its entirety). A single common light chain and two distinct heavy chains combine to form the bispecific. One of the heavy chains contains a substituted Fc sequence (hereinafter "Fc*") that reduces or eliminates binding of the Fc* to Protein A. For example, one such Fc* sequence contains H435R/Y436F (by EU numbering system; H95R/Y96F by IMGT exon numbering system) substitutions in the CH3 domain. As a result of co-expression of the two heavy chains and the common light chain, three products are created: two of which are homodimeric for the heavy chains and one of which is the desired heterodimeric bispecific product. The Fc* sequence allows selective purification of the FcFc* bispecific product on commercially available affinity columns, due to intermediate binding affinity for Protein A compared to the high avidity FcFc heavy chain homodimer, or the weakly binding Fc*Fc* homodimer.

To achieve commercial scale purification of the bispecific heterodimer, good resolution between the FcFc homodimer, the Fc*Fc heterodimer, and the Fc*Fc* homodimer is required. Here, Applicants describe an improved separation process that optimizes resolution of these three molecular forms.

SUMMARY

In one or more aspects and embodiments thereof, the invention is directed to methods of purifying a heterodimeric protein, such as for example a bispecfic antibody, from a complex mixture of proteins that include homodimers and heterodimers, by employing an affinity capture and elution process. In one aspect, the invention is directed to the purified heterodimeric protein produced by any one of these methods.

In a first aspect, the invention is directed to a method of making a protein comprising the steps of loading a mixture of multimeric proteins onto an affinity matrix, and then eluting and collecting a heterodimeric protein from that matrix at a particular pH range and in a buffer containing a chaotropic agent. In one embodiment, the affinity matrix is initially loaded with 5 to 50 grams of protein per liter of affinity matrix. In some cases, the mixture of multimeric proteins is produced by a plurality of eukaryotic cells, such as for example Chinese hamster ovary (CHO) cells in a cell culture.

In one embodiment, the mixture of multimeric proteins contains (i) a first homodimer comprising two copies of a first polypeptide, (ii) a heterodimer comprising the first polypeptide and a second polypeptide, and optionally (iii) a second homodimer comprising two copies of the second polypeptide. Here, the first and second polypeptides have different affinities for the affinity matrix, such that the first homodimer, the heterodimer and the second homodimer can be separated on the basis of differential binding to the affinity matrix.

Differential binding to an affinity matrix can be manipulated by changing inter alia the pH and/or ionic strength of a solution passed over the affinity matrix. The addition of the chaotropic agent to the solution enhances the elution each dimer species from the affinity matrix thereby increasing the purity of each individual dimer species. In one embodiment, the heterodimer is eluted from the affinity matrix in a buffer having a first pH range, and the first homodimer is eluted from the affinity matrix in a buffer having a second pH range. The heterodimer is collected. In an optional embodiment, in which the second homodimer is included in the mixture of multimers, the second homodimer either flows through the column without binding or is eluted from the affinity matrix in a wash buffer having a third pH range. The third pH range comprises a higher pH than the first pH range, which comprises a higher pH than the second pH range.

In one embodiment, the affinity matrix comprises a Protein A ligand affixed to a substrate. In some cases, the substrate is a bead or particle, such that the affinity matrix is a plurality of particles affixed with Protein A. The Protein A may be a naturally occurring or modified Staphylococcal Protein A, or it may be an engineered Protein A. Engineered Protein A may be for example a Z-domain tetramer, a Y-domain tetramer, or an engineered Protein A that lacks D and E domains. These engineered Protein A exemplars are unable to bind (or bind with very low affinity if at all) to the VH3 domain of an immunoglobulin, but can still bind to the CH3 domains of IgG1, IgG2 and IgG4.

In some cases, the affinity matrix substrate contains or is made of agarose, poly(styrene divinylbenzene), polymethacrylate, controlled pore glass, spherical silica, cellulose and the like. In the embodiments in which the substrate is shaped as a bead or particle, the mean diameter of the particles is from 25 µm to 100 µm. In some embodiments, the particles have a mean diameter of 35 µm, 45 µm, 60 µm, 75 µm, or 85 µm. In a particular embodiment, the particles have a mean diameter of 45 µm and contain pores having a mean diameter of 1100 Å.

In some embodiments, after the initial loading of the affinity matrix with the mixture of proteins, the matrix is washed with a buffer having a pH that is greater than pH 5. In some cases the buffer comprises 20 mM sodium phosphate at pH 7.2. When the second homodimer is included in the mixture of proteins, the second homodimer is washed from the affinity matrix in the wash buffer. Thus, here the wash buffer is of the third pH range.

In some embodiments, a buffered pH gradient is applied to the loaded affinity matrix, or in the alternative, sequential elution buffers, each having a different pHs are applied to the loaded affinity matrix. In one embodiment, the pH gradient is run from pH 6 to pH 3. The first pH range, within which the heterodimer is eluted from the affinity matrix, is about pH 5.5 to about pH 3.6. In some cases, the elution buffer and/or buffered pH gradient contains a suitable buffer, such as citrate, acetate, 4-Morpholineethanesulfonate (MES), citrate-phosphate, succinate, and the like, which in one embodiment is 40 mM acetate, and a chaotropic agent. The chaotropic agent can be a salt, having a cation selected from lithium, magnesium, calcium, and guanidinium, and an anion selected from chloride, nitrate, bromide, chlorate, iodide, perchlorate, and thiocyanate. In one particular embodiment, the chaotropic agent is CaCl$_2$, for example 250-500 mM CaCl$_2$. In another particular embodiment, the chaotropic agent is MgCl$_2$, for example 250-500 mM MgCl$_2$.

In one embodiment, the heterodimer is a bispecific antibody. Here, the first polypeptide comprises a CH3 domain that is capable of binding to Protein A ("Fc") and the second polypeptide comprises a CH3 domain that is not capable of binding to Protein A ("Fc*"). In some cases, the second polypeptide comprises a H435R/Y436F (by EU numbering system; H95R/Y96F by IMGT exon numbering system) substitution in its CH3 domain (a.k.a "Fc*" or "star substitution"). Thus, in some embodiments, the first homodimer is a monospecific antibody having two unsubstituted CH3 domains (i.e., FcFc); the second homodimer is a monospecific antibody having two H435R/Y436F substituted CH3 domains (i.e., Fc*Fc*); and the heterodimer is a bispecific antibody having one unsubstituted CH3 domain and one H435R/Y436F substituted CH3 domain (i.e., Fc*Fc).

In one embodiment, the heterodimer that is collected from the affinity matrix is subsequently loaded onto a chromatography medium at a more acidic pH, and eluted from that medium in a more alkaline buffer which lacks the chaotropic agent (or has a lower amount or trace amount of chaotrope). In one case, the chromatography medium is a multimodal chromatography resin. The heterodimer may be further purified.

In a second aspect, the second homodimer is first removed from the mixture of proteins by applying the mixture to a first affinity matrix such that the first homodimer and the heterodimer remain bound to the matrix while the second homodimer flows through and is discarded. The first homodimer and the heterodimer are subsequently eluted from the first affinity matrix and then subsequently applied to a second affinity matrix. In one embodiment, the first affinity matrix is initially loaded with 5 to 50 grams of protein per liter of affinity matrix. The mixture of multimeric proteins is produced in some cases by a plurality of eukaryotic cells, such as for example Chinese hamster ovary (CHO) cells in a cell culture.

In one embodiment, the mixture of multimeric proteins applied to the first affinity matrix contains (i) a first homodimer comprising two copies of a first polypeptide, (ii) a heterodimer comprising the first polypeptide and a second polypeptide, and (iii) a second homodimer comprising two copies of the second polypeptide. Here, the first and second polypeptides have different affinities for the first affinity matrix as well as for the second affinity matrix, such that the first homodimer, the heterodimer and the second homodimer can be separated on the basis of differential binding to the first and/or second affinity matrix.

In one embodiment, the first affinity matrix comprises an engineered Protein A ligand, which lacks the ability to bind the VH3 domain of an immunoglobulin, affixed to a substrate. In some cases, the protein A lacks a D-domain and an E-domain, such as the engineered proteins A that comprise a Z-tetramer or a Y-tetramer.

Differential binding of the first homodimer and the heterodimer to the second affinity matrix can be manipulated by changing inter alia the pH and/or ionic strength of a solution that is passed over the affinity matrix. The addition of a chaotropic agent to the solution enhances the elution each dimer species from the second affinity matrix in non-overlapping fractions, thereby increasing to purity of each dimer species. In one embodiment, the heterodimer is eluted from the second affinity matrix in a buffer having a first pH range, and the first homodimer is eluted from the second affinity matrix in a buffer having a second pH range. The heterodimer is collected. Here, the first pH range comprises a higher pH than does the second pH range.

In one embodiment, the second affinity matrix comprises a Protein A ligand affixed to a substrate. In some cases, the substrate is a bead or particle, such that the second affinity matrix is a plurality of particles affixed with Protein A ligand. The Protein A may be a naturally occurring or modified Staphylococcal Protein A, or it may be an engineered Protein A. Engineered protein A may be for example a Z-domain tetramer, a Y-domain tetramer, or another engineered Protein A that lacks D and E domains. These engineered protein A molecules are unable to bind (or bind with very low affinity if at all) to the VH3 domain of an immunoglobulin, but remain able to bind to the CH3 domains of IgG1, IgG2 and IgG4.

In some cases, the substrate contains or is made of agarose, poly(styrene divinylbenzene), polymethacrylate, controlled pore glass, spherical silica, cellulose (e.g., HYPERCEL) the like. In those embodiments in which the substrate is shaped as a bead or particle, the mean diameter of the particles is from 30 µm to 90 µm. In some embodiments, the particles have a mean diameter of 35 µm, 45 µm, 60 µm, 75 µm, or 85 µm. In a particular embodiment, the particles have a mean diameter of 45 µm and contain pores having a mean diameter of 1100 Å.

In some embodiments, after the initial loading of the second affinity matrix with the mixture containing the first homodimer and the heterodimer, the matrix is washed with a buffer having a pH that is greater than pH 5. In some cases the buffer comprises 20 mM sodium phosphate at pH 5-8.5, for example pH 7.2. In some embodiments, a buffered pH gradient is applied to the loaded affinity matrix, or in the alternative, sequential elution buffers, each having a different pHs are applied to the loaded second affinity matrix. In one embodiment, the pH gradient is run from pH 6 to pH 2.5. The first pH range, within which the heterodimer is eluted from the affinity matrix, is about pH 5.5 to about pH 3.6. In some cases, the elution buffer and/or buffered pH gradient contains acetate, which in one embodiment is 40 mM acetate, and a chaotropic agent. The chaotropic agent can be a salt, having a cation selected from lithium, magnesium, calcium, and guanidinium, and an anion selected from chloride, nitrate, bromide, chlorate, iodide, perchlorate, and thiocyanate. In one particular embodiment, the chaotropic agent is CaCl$_2$, for example 500 mM CaCl$_2$. In another particular embodiment, the chaotropic agent is MgCl$_2$, for example 500 mM MgCl$_2$.

In one embodiment, the heterodimer is a bispecific antibody. Here, the first polypeptide comprises a CH3 domain that is capable of binding to Protein A ("Fc") and the second polypeptide comprises a CH3 domain that is not capable of binding to Protein A ("Fc*"). In some cases, the second polypeptide comprises a H435R/Y436F (a.k.a. "star") substitution in its CH3 domain ("Fc*"). Thus, in some embodiments, the first homodimer is a monospecific antibody having two unsubstituted CH3 domains (i.e., FcFc); the second homodimer is a monospecific antibody having two H435R/Y436F substituted CH3 domains (i.e., Fc*Fc*); and the heterodimer is a bispecific antibody having one unsubstituted CH3 domain and one H435R/Y436F substituted CH3 domain (i.e., Fc*Fc).

In one embodiment, heterodimer that is collected from the second affinity matrix is subsequently loaded onto a chromatography medium at an acidic pH, and eluted from that medium in a more alkaline buffer and without the chaotropic agent (or reduced levels or trace amounts of chaotrope). In one case, the chromatography medium is a multimodal chromatography resin. The heterodimer may be further purified.

In a third aspect, the invention is directed to a purified heterodimer made according to the methods of the aspects described above. In one embodiment, the heterodimer is a bispecific antibody.

DETAILED DESCRIPTION

This invention is not limited to particular methods and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, particular methods and materials are now described. All publications mentioned are hereby incorporated by reference.

The term "antibody", as used herein, includes immunoglobulin molecules comprised of four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to those antibodies having a binding affinity to their target of at least $10^{-9}$ M, at least $10^{-1}$ M; at least $10^{-11}$ M; or at least $10^{-12}$ M, as measured by surface plasmon resonance, e.g., BIACORE™ or solution-affinity ELISA.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The phrase "heavy chain," or "immunoglobulin heavy chain" includes an immunoglobulin heavy chain constant region sequence from any organism, and unless otherwise specified includes a heavy chain variable domain. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an antigen (e.g., recognizing the antigen with a KD in the micromolar, nanomolar, or picomolar range), that is capable of expressing and secreting from a cell, and that comprises at least one CDR.

The phrase "light chain" includes an immunoglobulin light chain constant region sequence from any organism, and unless otherwise specified includes human kappa and lambda light chains. Light chain variable (VL) domains typically include three light chain CDRs and four framework (FR) regions, unless otherwise specified. Generally, a full-length light chain includes, from amino terminus to carboxyl terminus, a VL domain that includes FR1-CDR1-FR2-

CDR2-FR3-CDR3-FR4, and a light chain constant domain. Light chains that can be used with this invention include those, e.g., that do not selectively bind either the first or second antigen selectively bound by the antigen-binding protein. Suitable light chains include those that can be identified by screening for the most commonly employed light chains in existing antibody libraries (wet libraries or in silico), where the light chains do not substantially interfere with the affinity and/or selectivity of the antigen-binding domains of the antigen-binding proteins. Suitable light chains include those that can bind one or both epitopes that are bound by the antigen-binding regions of the antigen-binding protein.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4. A "variable domain" includes an amino acid sequence capable of folding into a canonical domain (VH or VL) having a dual beta sheet structure wherein the beta sheets are connected by a disulfide bond between a residue of a first beta sheet and a second beta sheet.

The phrase "complementarity determining region," or the term "CDR," includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The term "star substitution", "Fc*", and "HC*" includes any molecule, immunoglobulin heavy chain, Fc fragment, Fc-containing molecule and the like which contain a sequence within the CH3 domain that abrogates binding to Protein A. It has been previously noted (Lindhofer, H. et ai (1995) J. Immunol. 155:219-225)) that because human IgG3 does not to bind to Protein A, it can potentially be used together with any of the other three human IgG subclasses in a purification strategy similar to the one used for mouse-rat hybrids. However, although the sequences of all four human IgG subclasses are highly homologous, it is not known how readily the Fc portions of IgGI, IgG2, and IgG4 form heterodimers with IgG3; even merely preferential formation of homodimers would have a negative impact on total yields of the desired heterodimers under certain circumstances (e.g., isolation from quadromas). It has been reported (Jendeberg, L. et al. (1997) J. Immunological Meth. 201:25-34)) that the inability of IgG3 to bind Protein A is determined by a single amino acid residue, Arg435 (EU numbering; Arg95 by IMGT), which corresponding position in the other IgG subclasses is occupied by a histidine residue. It is therefore possible, instead of IgG3, to use an IgG1 sequence in which His435 is mutated to Arg. Thus, a single point mutation in IgG1 should be sufficient to create the different binding affinities amenable to a new purification scheme. This modification will be referred to as IgGI ΔA, to denote its inability to bind Protein A (and, similarly, IgG2ΔA and IgG4ΔA—or more generally, FcΔA).

However, the specified point mutation introduces a novel peptide sequence across the mutation, which could potentially be immunogenic. The point mutation could, in theory, be loaded onto an MHC class Il molecule and presented to T cells, and consequently elicit an immune response. To avoid this pitfall, a dipeptide mutation, H435R/Y436F (EU numbering; H95R/Y96F by IMGT) can be used. The resulting sequence in the vicinity of the alteration is identical to that of IgG3, and would therefore be expected to be immunologically "invisible," because there would be no non-native short peptides available for presentation to T cells. It has been reported that this double mutant still does not bind Protein A (Jendeberg, L. et al. (1997) J. Immunological Meth. 201:25-34). Finally, the dipeptide mutation does not include any of the residues that form the Fc dimer interface, so it is unlikely to interfere with the formation of heterodimers. This dipeptide mutation is designated as the "star substitution".

The term "cell" includes any cell that is suitable for expressing a recombinant nucleic acid sequence. Cells include those of prokaryotes and eukaryotes (single-cell or multiple-cell), bacterial cells (e.g., strains of E. coli, Bacillus spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g. a retinal cell that expresses a viral gene (e.g., a PER.C6™ cell).

The phrase "mobile phase modifier" includes moieties that reduce the effect of, or disrupt, non-specific (i.e., non-affinity) ionic and other non-covalent interactions between proteins. "Mobile phase modifiers" include, for example, salts, ionic combinations of Group I and Group II metals with acetate, bicarbonate, carbonate, a halogen (e.g., chloride or fluoride), nitrate, phosphate, or sulfate. A non-limiting illustrative list of "mobile phase modifiers" includes beryllium, lithium, sodium, and potassium salts of acetate; sodium and potassium bicarbonates; lithium, sodium, potassium, and cesium carbonates; lithium, sodium, potassium, cesium, and magnesium chlorides; sodium and potassium fluorides; sodium, potassium, and calcium nitrates; sodium and potassium phosphates; and calcium and magnesium sulfates.

"Mobile phase modifiers" also include chaotropic agents, which weaken or otherwise interfere with non-covalent forces and increase entropy within biomolecular systems. Non-limiting examples of chaotropic agents include butanol, calcium chloride, ethanol, guanidinium chloride, lithium perchlorate, lithium acetate, magnesium chloride, phenol, propanol, sodium dodecyl sulfate, thiourea, and urea. Chaotropic agents include salts that affect the solubility of proteins. The more chaotropic anions include for example chloride, nitrate, bromide, chlorate, iodide, perchlorate, and thiocyanate. The more chaotropic cations include for example lithium, magnesium, calcium, and guanidinium.

"Mobile phase modifiers" include those moieties that affect ionic or other non-covalent interactions that, upon addition to a pH gradient or step, or upon equilibration of a Protein A support in a "mobile phase modifier" and application of a pH step or gradient, results in a broadening of pH unit distance between elution of a homodimeric IgG and a heterodimeric IgG (e.g., a wild-type human IgG and the same IgG but bearing one or more modifications of its CH3 domain as described herein). A suitable concentration of a "mobile phase modifier" can be determined by its concentration employing the same column, pH step or gradient, with increasing concentration of "mobile phase modifier" until a maximal pH distance is reached at a given pH step or pH gradient. "Mobile phase modifiers" may also include non-polar modifiers, including for example propylene glycol, ethylene glycol, and the like.

As used herein, "affinity chromatography" is a chromatographic method that makes use of the specific, reversible interactions between biomolecules rather than general properties of the biomolecule such as isoelectric point, hydrophobicity, or size, to effect chromatographic separation.

"Protein A affinity chromatography" or "Protein A chromatography" refers to a specific affinity chromatographic method that makes use of the affinity of the IgG binding domains of Protein A for the Fc portion of an immunoglobulin molecule. This Fc portion comprises human or animal immunoglobulin constant domains CH2 and CH3 or immunoglobulin domains substantially similar to these. Protein A encompasses native protein from the cell wall of *Staphylococcus aureus*, Protein A produced by recombinant or synthetic methods, and variants that retain the ability to bind to an Fc region. In practice, Protein A chromatography involves using Protein A immobilized to a solid support. See Gagnon, Protein A Affinity Chromotography, Purification Tools for Monoclonal Antibodies, pp. 155-198, Validated Biosystems, 1996. Protein G and Protein L may also be used for affinity chromotography. The solid support is a non-aqueous matrix onto which Protein A adheres. Such supports include agarose, sepharose, glass, silica, polystyrene, nitrocellulose, charcoal, sand, cellulose and any other suitable material. Such materials are well known in the art. Any suitable method can be used to affix the second protein to the solid support. Methods for affixing proteins to suitable solid supports are well known in the art. See e.g. Ostrove, in Guide to Protein Purification, Methods in Enzymology, 182: 357-371, 1990. Such solid supports, with and without immobilized Protein A, are readily available from many commercial sources including such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden), Pall (Port Washington, N.Y.) and EMD-Millipore (Billerica, Mass.). Protein A immobilized to a pore glass matrix is commercially available as PROSEP®-A (Millipore). The solid phase may also be an agarose-based matrix. Protein A immobilized on an agarose matrix is commercially available as MABSELECT™ (Amersham Biosciences).

Affinity chromatography also includes media that can be used to selectively bind and thus purify antibodies, fragments of antibodies, or chimeric fusion proteins that contain immunoglobulin domains and/or sequences. Antibodies include IgG, IgA, IgM, IgY, IgD and IgE types. Antibodies also include single chain antibodies such as camelid antibodies, engineered camelid antibodies, single chain antibodies, single-domain antibodies, nanobodies, and the like. Antibody fragments include VH, VL, CL, CH sequences. Antibody fragments and fusion proteins containing antibody sequences include for example F(ab')$_3$, F(ab')$_2$, Fab, Fc, Fv, dsFv, (scFv)$_2$, scFv, scAb, minibody, diabody, triabody, tetrabody, Fc-fusion proteins, trap molecules, and the like (see Ayyar et al., Methods 56 (2012): 116-129). Such affinity chromatography media may contain ligands that selectively bind antibodies, their fragments, and fusion proteins contains those fragments. Such ligands include antibody binding proteins, bacterially derived receptors, antigens, lectins or anti-antibodies directed to the target molecule. the antibody requiring purification. For example, camelid-derived affinity ligands directed against any one or more of IgG-CH1, IgG-Fc, IgG-CH3, IgG1, LC-kappa, LC-lambda, IgG3/4, IgA, IgM, and the like may be used as affinity ligands (commercially available as CAPTURESELECT chromatography resins, Life Technologies, Inc., Carlsbad, Calif.)

Example 1: Peak Resolution Process

Bispecific antibodies were separated from the contaminating homodimers via Protein A chromatography utilizing the star substitution as follows. Since Fc*Fc* homodimer has both Protein A binding sites deleted from the Fc region, this product-related impurity was expected to flow though the column and be removed while the bispecific and FcFc homodimer was expected to be retained on the column. A series of washes was applied to remove process-related contaminants such as CHO DNA or host cell protein (HCP). The bispecific was then selectively eluted via a pH gradient or step while the FcFc contaminant was retained due to its stronger binding relative to the bispecific.

Figure 1:
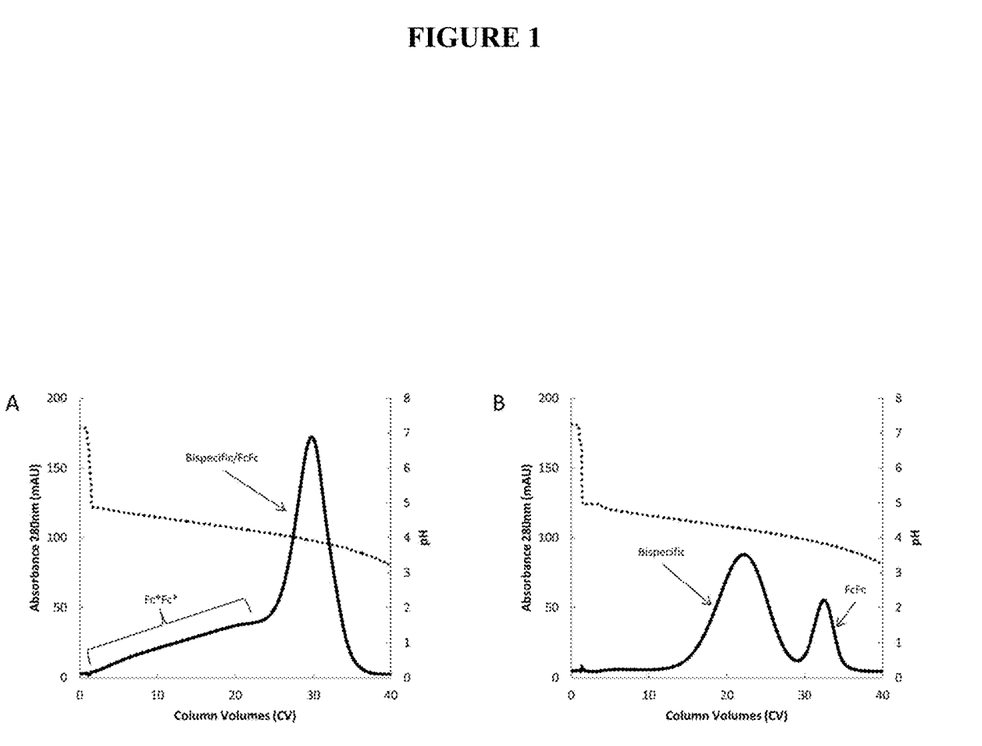
FIG. 1 depicts chromatograms illustrating pH (dotted) and absorbance at 280 nm (solid) during elution step for purification of bsAb E with a recombinant Protein A resin (MABSELECT XTRA™, panel A), and an engineering Protein A-based resin which lacks VH binding (MABSELECT SURE™, panel B).

Wide variability in separation performance from bispecific to bispecific was observed when initial experiments were performed using a recombinant Staphylococcal Protein A (SpA) chromatography resin. Whereas baseline resolution between the binding FcFc homodimers and the bispecific product was obtained in some cases, a subgroup of bispecific antibodies ("bsAbs") exhibited very poor resolution. For these molecules, good resolution was attainable when performing the separation on an affinity resin engineered to exhibit improved base stability. One example of this is bsAb E, for which harvested clarified cell culture fluid was loaded to 5 g/L on either a SpA resin (MABSELECT XTRA™, FIG. 1A) or an engineered Protein A-based resin (MABSELECT SURE™, FIG. 1B). After a series of (e.g., pH 6-8) buffer wash steps, a 40 column volume ("CV") gradient from pH 5 to 3 in 40 mM acetate 500 mM NaCl was applied to elute the bound species. On MABSELECT XTRA™ (FIG. 1A) an elution peak between 25-35 CV contained both the bispecific and the FcFc homodimer with no resolution. Furthermore, despite the lack of Protein A binding in the Fc region of the Fc*Fc* contaminant, a leading shallow elution peak (0-25 CV) consisted of the Fc*Fc* homodimer Protein. However, the same bsAb E load applied to MABSELECT SURE™ yielded two well resolved peaks containing the bispecific and FcFc homodimer, respectively (FIG. 1B), with all the Fc*Fc* homodimer flowing through the column during the load. This may be caused by the different interactions between IgG and native Protein A ("SpA") and the engineered SuRe ligand.

In addition to the classical binding site, some antibodies have been shown to contain an alternative SpA binding site on the variable region of the heavy chain ("VH"). In particular, some IgGs that contain heavy chains from the human VH3 gene family have been shown to exhibit this behavior, with nearly half of human VH germline genes belonging to the VH3 subfamily. (See Sasso et al., Journal of Immunology 1989; 142:2778-83; Sasso et al., Journal of Immunology 1991; 147:1877-83; Schroeder et al., International Immunology 1990; 2:41-50; and Walter, M. A., and D. W. Cox, American Journal of Human Genetics 1988; 42:446-51.) Therefore it appears likely that on SpA-based resins, bispecific antibodies such as bsAb E exhibit poor resolution of the two binding species and retention of the "non-binding" Fc*Fc* homodimer resins due to VH binding. The VH binding is thus thought to reduce the avidity difference between the bispecific, and the FcFc homodimer, and the low affinity binding of Fc*Fc*.

This hypothesis is supported by the improved purification observed with MABSELECT SURE™. Binding studies between SpA and antibodies have shown that while all five domains of SpA (E, D, A, B and C) bind IgG via the Fc-region, only domains D and E exhibit significant Fab binding. (See e.g., Starovasnik et al., Protein Science 1999; 8:1423-31). The engineered MABSELECT SURE™ affinity ligand is a tetramer of the Z-domain, a protein-engineered version of the native, non-Fab binding SpA B domain. The Z-domain is known to have negligible binding to the antibody variable region (Starovasnik, supra). Therefore when this resin carrying the MABSELECT SURE™ ligand is used, the increased difference in avididty between the bispecific and the FcFc homodimer allows for improved resolution of those peaks; and the Fc*Fc* homodimer is not retained.

Multiple Protein A-based chromatographic resins were screened in order to identify a resin for bispecific clinical and commercial production. Two bsAbs were chosen for evaluation, one previously observed to bind SpA via the VH region (bsAb A) and one lacking this capability (bsAb B). The load material was previously subjected to standard positive mode affinity chromatography to remove the Fc*Fc* impurity. Starting bispecific purities (Fc*Fc/[Fc*Fc+Fc*Fc*+FcFc]) were 84% and 76% for bsAb A and bsAb B respectively. All resins were loaded to 10 g total protein/L resin. After a series of washes the antibodies were eluted using a 30 CV gradient from pH 6 to 3 with either 500 mM NaCl or 500 mM CaCl$_2$ as mobile phase modifiers.

The six selected commercially available Protein A resins exhibit a variety of base matrices, bead sizes and ligand types. Four of the resins used SpA, one was a tetramer of the Z-domain (MABSELECT SURE™), and one was a multimer of a base stabilized version of the non-Fab binding C domain, termed the Y-domain (TOYOPEARL AF-rProtein A-650F). These data and the peak resolution (Rs=1.18([t$_{R2}$-t$_{R1}$]/[W½$_2$+W½$_1$]; wherein Rs is peak resolution, W½ peak width at half height, and t$_R$ is retention time) obtained between the bispecific product and the binding FcFc homodimer are detailed in Table 1.

TABLE 1

Comparison of separation efficiency of bispecific from binding impurity obtained using a range of Protein A media with two antibodies: V$_H$-Protein A binding (bsAb A) and non-V$_H$ binding (bsAb B).

| | | | | Resolution Obtained[a] (Rs) | | |
|---|---|---|---|---|---|---|
| Resin | Average Particle Size (μm) | Base Matrix | Protein A Origin | bsAb A (modifier: NaCl) | bsAb A (modifier: CaCl$_2$) | bsAb B (modifier: NaCl) |
| MABSELECT SURE | 85 | Agarose | Tetramer of z-domain (modified B domain) | 0.92 | 1.08 | N/M |
| POROS MABCAPTURE | 45 | Poly(styrene divinylbenzene) | Recombinant | 0.70 | 1.83 | 2.50 |

TABLE 1-continued

Comparison of separation efficiency of bispecific from binding impurity obtained using a range of Protein A media with two antibodies: $V_H$-Protein A binding (bsAb A) and non-$V_H$ binding (bsAb B).

| Resin | Average Particle Size (μm) | Base Matrix | Protein A Origin | Resolution Obtained[a] (Rs) | | |
|---|---|---|---|---|---|---|
| | | | | bsAb A (modifier: NaCl) | bsAb A (modifier: CaCl$_2$) | bsAb B (modifier: NaCl) |
| A TOYOPEARL AF-rProtein A-650F | 45 | Polymethacrylate | Tetramer of y-domain (modified C domain) | 0.87 | N/M | 2.37 |
| ProSep Ultra Plus Affinity | 60 | Controlled Pore Glass | Recombinant | No resolution | N/M | N/M |
| AbSolute High Cap | 35 | Spherical Silica, modified for high pH resistance | Recombinant | 0.49 | N/M | 2.41 |
| MabSelect Xtra | 75 | Agarose | Recombinant | No resolution | N/M | N/M |

[a]Resolution calculated using width at half height. If peak width at half height could not be calculated due to peak convergence, resolution marked as "no resolution".

When using NaCl as a mobile phase modifier in the elution buffer, increased resolution was noted in inverse proportion to bead size, with no resolution observed for SpA resins with a mean particle greater than 45 μm. Interestingly MABSELECT SURE™ (Rs=0.92) showed comparable performance to TOYOPEARL AF-rProtein A-650F (Rs=0.87) with bsAb A. This was not expected due to (i) the smaller average bead size for TOYOPEARL AF-rProtein A-650F (45 cf. 85 μm) and (ii) the similarity of the affinity ligand, which is based on the Y-domain (derived from the C domain) and thus expected to lack VH binding (Starovasnik, supra). For bsAb B, POROS MABCAPTURE A™ exhibited superior resolution as compared to TOYOPEARL AF-rProtein A-650F and ABSOLUTE HICAP™ (2.50 compared to 2.37 and 2.41, respectively), despite not having the smaller particle size. This was hypothesized to be due to the element of perfusive flow in this base matrix, facilitated by the large through pores, and mean pore diameter of 1100 Angstroms, aiding mass transfer. POROS MABCAPTURE A™ also exhibited better resolution of bsAb A than did any other SpA resin, with comparable resolution to the non-VH binding resins of TOYOPEARL AF-rProtein A-650F and MABSELECT SURE™ (0.70 compared to 0.87 and 0.92 respectively).

When NaCl was replaced with CaCl$_2$ as the mobile phase modifier, POROS MABCAPTURE A™ was observed to greatly improve resolving power, outperforming MABSELECT SURE™ by a considerable margin (Rs of 1.83 c.f. 1.08, respectively). Based on the totality of this data, POROS MABCAPTURE A™ and MABSELECT SURE™ were evaluated further as possible resolving chromatographic resins for isocratic elution.

Figure 2:
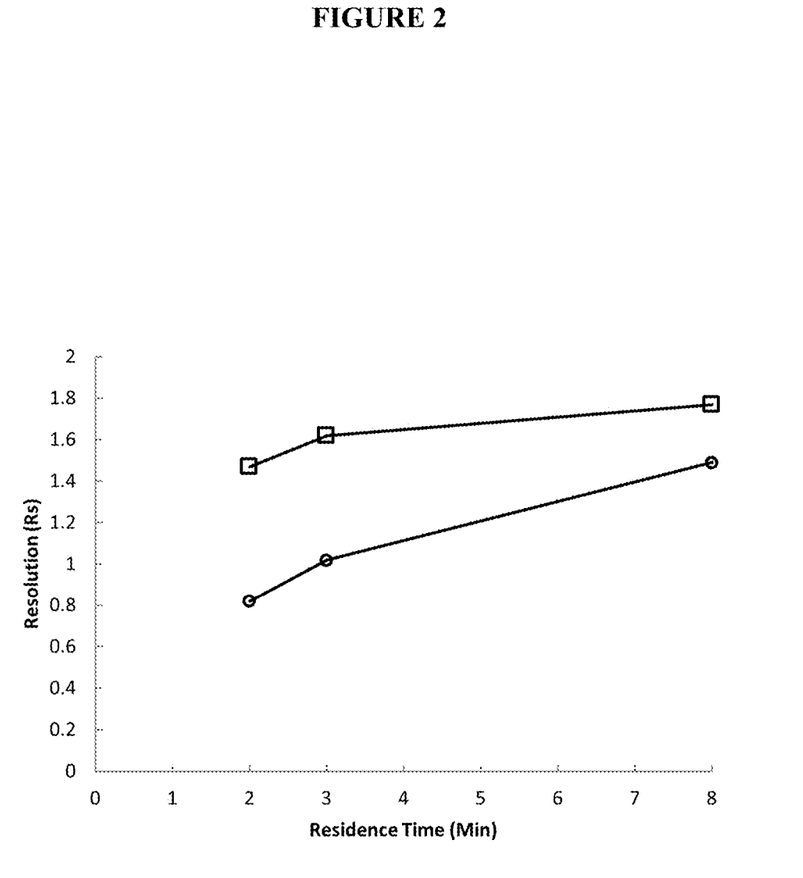
FIG. 2 depicts the peak resolutions (Rs) obtained between the bispecific (Fc*Fc) and non-CH3-substituted homodimer (FcFc) peaks as a function of residence time during a 30 column volume ("CV") gradient elution in 40 mM acetate, 500 mM calcium chloride with either MABSELECT SURE™ (open circles), or POROS MABCAPTURE A™ (closed squares) as the stationary phase.

Since the resin comparison was performed at a relatively fast linear velocity of 400 cm/h, the MABSELECT SURE resin could have been reduced in efficacy relative to POROS MABCAPTURE A because of (i) the larger bead size and (ii) lack of perfusive flow. The resins were therefore compared at a production relevant range of residence times. BsAb A was selected as the model molecule due to its observed binding to SpA via its VH region (thereby giving a greater avidity difference between the bispecific and FcFc impurity to the non-VH binding MABSELECT SURE). Note a VH binding antibody was chosen for this evaluation, as without this avidity advantage MABSELECT SURE would be expected to be inferior due to the smaller bead size of MABCAPTURE A. The same affinity captured bsAb A load material as used for the resin evaluation study was used, at a 10 g total protein/L resin challenge. All chromatographic steps were performed at a 3 minute residence time with the exception of the elution, which was varied from 2-8 minutes (600-150 cm/h). Calculation of the resolution of the bispecific peak from the FcFc homodimer peak showed that although the resolution of the resins increased with residence time, the effect was more pronounced for MABSELECT SURE than POROS MABCAPTURE A (Rs increase of 0.7 and 0.3, respectively, FIG. 2). Additionally, the POROS MABCAPTURE A resin showed superior resolution to MABSELECT SURE at all tested conditions, despite the disadvantage of VH binding for this resin, confirming the overall superiority of the resin with regards to resolving power of the two binding species.

Figure 3:
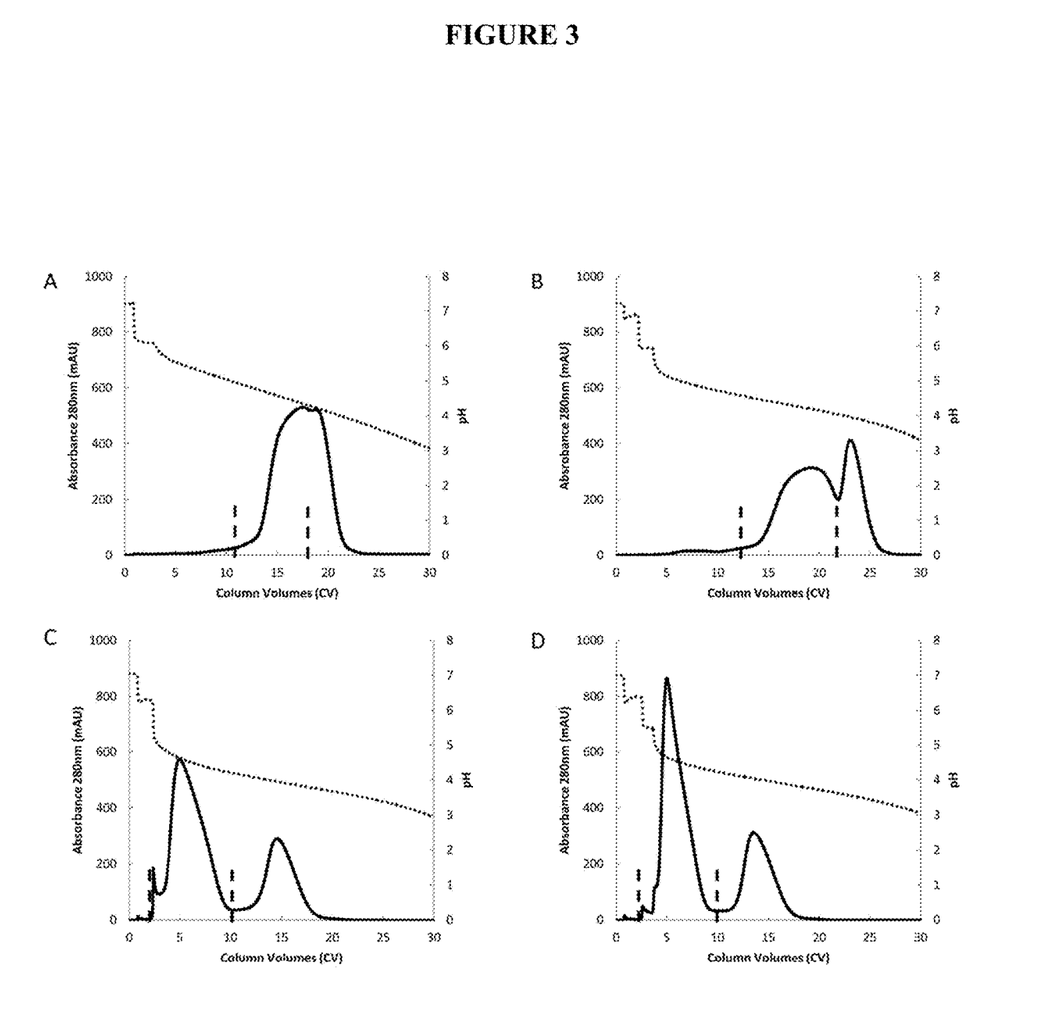
FIG. 3 depicts chromatograms illustrating pH (dotted) and absorbance at 280 nm (solid) during elution step for purification of bsAb A with either sodium citrate (panel A), sodium chloride (panel B), magnesium chloride (panel C), or calcium chloride (panel D) added as modifiers to the elution mobile phase. Bispecific peak fractionation is marked by vertical dotted lines.

The inclusion of mobile phase modifiers in the elution buffer altered and potentially improved the resolution of the bispecific product from the FcFc homodimer (see Table 1). Thus, the use of salts of varying position on the Hofmeister series was hypothesized to improve resin selectivity by moderation of hydrophobic interactions between the antibody species and the Protein A ligand. The VH-binding bsAb A was loaded at 10 g/L on MABCAPTURE A resin. Following a series of washes the antibodies were eluted using a 30 CV gradient from pH 6 to 3 with the following elution mobile phase modifiers: sodium citrate, sodium chloride, magnesium chloride, and calcium chloride, ranked in order from kosmotroph to chaotroph in the Hofmeister series. A salt level of 500 mM was used for all salts but sodium citrate, where 250 mM was used due to protein precipitation in the load material when spiked to concentrations above 300 mM. Superior resolution between the bispecific product and the binding FcFc homodimer was obtained with more the chaotropic salts (FIG. 3). Bispecific peaks were collected from first peak liftoff, to peak valley inflexion as detailed in FIG. 3. Percent bispecific yield, percent bispecific purity, peak resolution (Rs) and percent soluble aggregate were measured (Table 2). The pH at bispecific pH apex was also calculated from the chromatograms. The use of the more chaotropic salts (calcium chloride and magnesium chloride) exhibited increased yield and bispecific purity. Protein was also eluted at a higher pH with magnesium chloride and calcium chloride. Neither the most chaotropic nor the most kosmotropic salts used induced significant aggregation during elution of the bispecific. Therefore the use of chaotropic salts such as calcium chloride as mobile phase modifiers in the elution buffer was shown to enhance the peak resolution and the subsequent purification of bsAb.

TABLE 2

Yield, soluble aggregate, peak apex pH, peak resolution and bispecific purity measured in bispecific fractions collected during gradient elution of bsAb A from POROS MABCAPTURE A ™ using a variety of elution mobile phase modifiers.

| Elution Modifier | Bispecific Peak Apex pH | Bispecific Yield (%) | Bispecific Purity (%) | Pool Soluble Aggregate (%) | Resolution Obtained (Rs) |
| --- | --- | --- | --- | --- | --- |
| Sodium Citrate | 4.4 | 83 | 79 | 1.9 | No resolution |
| Sodium Chloride | 4.2 | 67 | 97 | N/M | 0.54 |
| Magnesium Chloride | 4.6 | 76 | 97 | N/M | 1.66 |
| Calcium Chloride | 4.6 | 100 | 100 | 0.79 | 1.83 |

Example 2: Development of a Commercial Process

In order to determine feasibility of a star substitution based platform for purification of bispecific antibodies, a scalable process for the purification of bsAb C was developed. This protein was chosen as a worst-case test for the platform as it was found to display significant VH binding to SpA. The key developmental goal were: (i) achieve isocratic (step) elution to simplify plant fit and technology transfer while also reducing buffer consumption and processing time, (ii) identify polishing step interfacing with affinity resolving step with little or no load conditioning.

Initial factor screening and design space evaluation was performed using high throughput screening in the 96-well plate format (HTPD). Elution pH, column loading (g/L total protein) and mobile phase modifier concentration were identified as key process inputs (see FIG. 2). Elution residence time was also considered. The load material for this study had been previously subjected to standard positive mode affinity chromatography to remove the Fc*Fc* impurity, resulting in a 64% bispecific purity. Two 18-run central-composite design-of-experiments studies (CCD DoE) were performed in order to evaluate both MABSELECT SURE and POROS MABCAPTURE A in an isocratic elution mode. Factors studied for POROS MABCAPTURE A resin were column loading (range 10-25 g total protein/L), elution pH (4.5-5.5) and concentration of calcium chloride in the elution buffer (250-500 mM). Residence time was held constant at 3 min (400 cm/h). MABSELECT SURE was then evaluated in terms of column loading (range 10-25 g total protein/L), elution pH (3.8-5.0) and elution residence time (5-11 min). Calcium chloride concentration in the elution buffer was held constant at 500 mM.

For MABCAPTURE A, good models were obtained for both bispecific yield ($R^2$=0.97) and bispecific purity ($R^2$=0.92) using a standard least squares fit algorithm. At all conditions, increasing calcium chloride levels from 250-500 mM in the elution buffer were observed to increase bispecific yields by 10-20% without reducing bispecific purity (data not shown). Using the model, a sweet spot analysis was conducted at 500 mM $CaCl_2$. The analysis illustrated that an elution pH of 5.0-5.1 would allow purity goals of >95% and yield of >80% to be met with a resin challenge of 17-25 g/L. Similar chromatographic conditions have been used at up to 2 kL production scale, and bispecific purities in excess of 99% have been obtained after further optimization.

Evaluating MABSELECT SURE data, good model fits were attained for bispecific yield ($R^2$=0.99) and bispecific purity ($R^2$=1.00). Residence time was not shown to be a significant factor for either response. As for MABCAPTURE A, constraints were imposed on contour plots at an 8 minute residence time to exclude regions where bispecific yield <80% and bispecific purities <95% were obtained. The desirable operating window or sweet spot is much smaller than observed with MABCAPTURE A. Therefore the use of MABSELECT SURE may result in a process exhibiting insufficient robustness at production scale, as small pH or loading changes may result in unacceptable bispecific purities or yields.

Example 3: Post-Affinity Polishing

Following the affinity resolving step, the bispecific antibody may be subjected to polishing steps intended to remove process and product related impurities in a fashion highly similar to standard monoclonal antibodies. However, the use of a high concentration of calcium chloride in the elution buffer of the resolving affinity step might potentially complicate downstream unit operations. An ultrafiltration/diafiltration (UF/DF) could be used to reduce the conductivity of the pool in order to facilitate traditional mAb polishing steps, such as cation exchange or anion exchange chromatography. However, identification of a salt tolerant positive mode chromatographic step could avoid introduction of this additional unit operation. Multimodal or mixed mode chromatography combines various types of interactions such as hydrophobic interaction, hydrogen bonding and ionic interaction with a single resin. It has been noted that this can facilitate salt tolerant adsorption.

A variety of multimodal resins were considered as polishing steps: (i) CAPTO ADHERE and (ii) CAPTO ADHERE IMPRES (the N-benzl-methyl ethanol amine ligand of both of these contains anion exchange, hydrophobic and hydrogen bonding interaction groups), (iii) ceramic hydroxyapatite and (iv) CAPTO MMC, a multimodal cation exchange resin with hydrophobic interaction and hydrogen bonding potential. Ultimately, CAPTO MMC was developed to simultaneously remove process- and product-related impurities while lowering process stream conductivity. Following process development, proof-of-concept has been confirmed at manufacturing scale utilizing positive mode CAPTO MMC chromatography with bsAb C and bsAb D (see Table 3). In both instances reasonable (19-25 g/L) dynamic binding capacity was obtained with yields ≥85%, up to 3-fold reduction in soluble aggregate, and moderate (0.2-0.7 log removal) CHO host cell protein clearance.

TABLE 3

Yield and contaminant removal obtained by positive mode multimodal chromatography using CAPTOMMC media loaded with affinity resolving pool containing 250 mM $CaCl_2$.

| Bispecific Molecule | Column Loading (g total protein/L) | Load Soluble Aggregate (%) | Pool Soluble Aggregate (%) | HCP Removal (LRV) | Yield (%) |
|---|---|---|---|---|---|
| bsAb C | 19 | 2.4 | 0.7 | 0.7 | 96 |
| bsAb D | 23 | 12.6 | 4.8 | 0.2 | 85 |

Example 4: Purification Strategies

Figure 4:
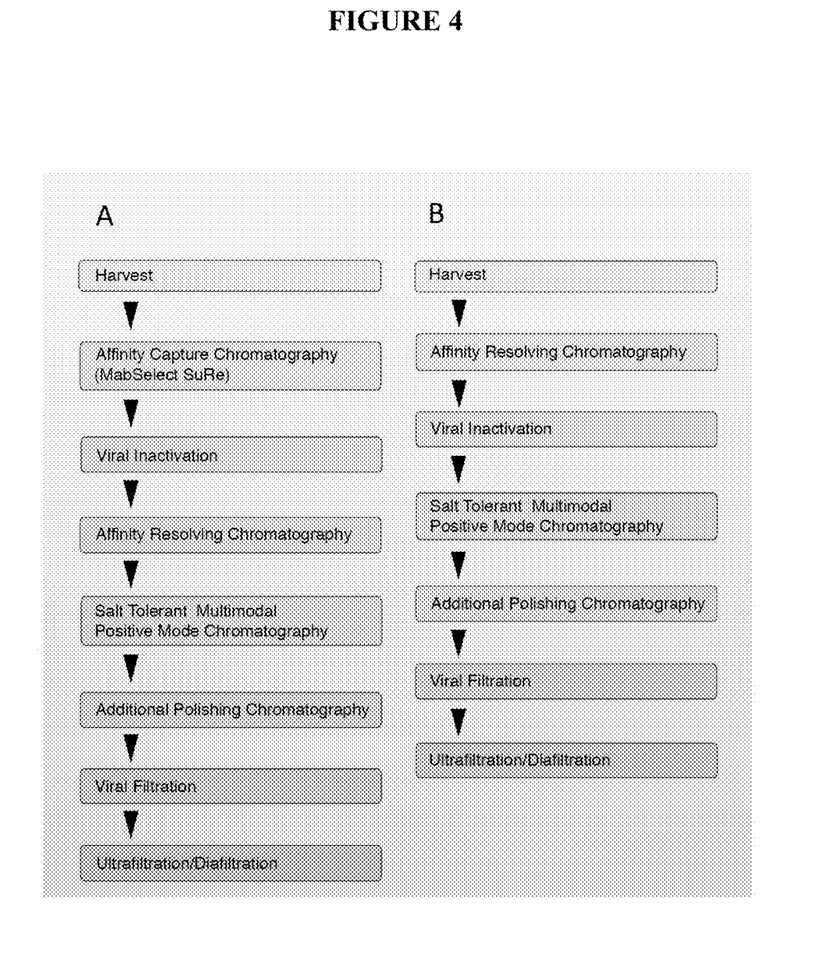
FIG. 4 depicts the flow scheme of purification processes for star substitution-containing (CH3-substituted, Fc*) bispecific antibodies (Fc*Fc) exhibiting (panel A) and not exhibiting (panel B) VH domain SpA binding.

Based on the discoveries made and described above, two downstream bispecific process platforms are envisioned (FIG. 4). If the bispecific antibody is derived from the VH3 gene fragment family and is capable of binding SpA through the VH region, an additional affinity chromatography unit operation, termed affinity capture chromatography may be employed (FIG. 4A). After removal of cells and debris by harvest, affinity capture chromatography is performed using MABSELECT SURE resin, since the lack of VH binding via the Z-domain ensures removal of the Fc*Fc* parental antibody impurity. This step can be performed using Protein A binding, wash and elution conditions standard to commercial monoclonal antibodies and also acts to increase protein concentration and remove process- and product-related impurities. As the protein is eluted at low pH it is also convenient to perform a low pH hold for viral inactivation with the product pool. Following this, removal of the FcFc impurity is achieved by a second positive mode Protein A step termed "affinity resolving chromatography". The use of POROS MABCAPTURE A resin coupled with chaotropic modifiers in the elution buffer can result in pools of >95% bispecific purity. After affinity resolving chromatography, the use of positive mode salt tolerant multimodal chromatography facilitates direct interfacing with the affinity resolving step thus obviating the need for an intervening UF/DF operation to remove the chaotropic salt from the process stream. Coupled with an additional polishing step such as anion exchange chromatography and virus retentive filtration, aggregates, HCP, DNA, viruses and other impurities can be removed to acceptable levels. Finally, the purified product is concentrated into the final formulation buffer by standard ultrafiltration/diafiltration methodologies. This purification train can be simplified if the bispecific molecule does not exhibit VH binding to SpA by removal of the affinity capture step (FIG. 4B). In this case, removal of both the FcFc and the Fc*Fc* impurities can be performed by affinity resolving chromatography.

Example 5: Materials and Methods

All bispecific antibodies and cell culture fluid used in these examples were expressed in CHO cells. Chromatographic resins were acquired from their manufacturers: MABSELECT SURE, MABSELECT XTRA, CAPTO MMC (GE Healthcare), POROS MABCAPTURE A (Life Technologies), TOYOPEARL AF-rProtein A-650F (TOSOH Biosciences), ABSOLUTE HIGH CAP (Novasep Inc.), PROSEP ULTRA PLUS (EMD Millipore). All chemicals used were supplied by J. T. Baker.

Lab scale chromatographic separations were performed using an AKTA AVANT chromatographic system from GE Healthcare and 1.0 cm inner diameter (I.D.) OMNIFIT BENCHMARK chromatography columns (Omnifit Ltd). Pilot scale chromatography applied AKTA PILOT chromatographic systems and 7.0 cm I.D. INdEX chromatography columns from GE Healthcare. Production scale chromatography was conducted on an AKTAPROCESS chromatography skid and 40 cm I.D. CHROMOFLOW columns (GE Healthcare). UPLC analysis leveraged an ACQUITY UPLC system from Waters Corporation. Cell culture was performed using either a 2L BIOSTAT B-DCU bench top bioreactor (Sartorius), a 50, 250, or 2000L HYCLONE single use bioreactor (Thermo Scientific), or a 160L stainless steel bioreactor (ABEC Inc.).

When clarified cell culture fluid was not used directly, load material for affinity resolving development was produced by affinity capture chromatography using 20±1 cm bed height MABSELECT SURE columns. After equilibration with two column volumes (CVs) of 20 mM sodium phosphate pH 7.2 the columns were loaded to 10-40 g binding antibody/L with clarified cell culture fluid. Binding antibody concentration was determined by summation of the bispecific and FcFc titers. Columns were washed and protein eluted with a proprietary buffer system before a 2 CV column strip. The entire elution peak was collected and neutralized to pH 7.5±0.5 with 2M Tris base.

All affinity resolving chromatography was performed using 20±1 cm bed height columns. The Protein A columns studied were equilibrated with two CVs 20 mM sodium phosphate pH 7.2 before load application. Following loading, columns were washed with a proprietary wash buffer system and eluted with either a gradient or isocratic elution as specified. For isocratic runs a four CV elution volume was used, collecting pool from 0.5-4 CVs after initiation of the elution step. Both gradient and isocratic elution buffers contained 40 mM acetate as the buffering species. Following elution columns were stripped with 2 CV of buffer. Unless otherwise stated all steps were performed at a linear velocity of 400 cm/h. UNICORN 6.1 software (GE Healthcare) was used for chromatographic analysis, including calculation of peak resolution (Rs) assuming Gaussian peaks using the width at half height method. When automated fractionation was performed, peak liftoff was defined by >50 mAu increase in baseline UV280. Statistical design of experiments, analysis and modeling was performed using JMP 11.1.1 (SAS Institute Inc.).

CAPTO MMC chromatography was performed using 25.1 L columns (20 cm bed height; 40 cm I.D.) with all steps performed at a 4 min residence time (linear velocity 300 cm/h). Affinity resolving pools were diluted 50% with water and adjusted to pH 5.0±0.1. The columns were pre-equilibrated with 2 CV of 2 M NaCl before a 2 CV equilibration in 40 mM sodium acetate, 250 mM calcium chloride, pH 5.0±0.1. After load application the columns were washed with 3 CV of 40 mM Tris, 40 mM acetate, pH 5.0±0.1 and product was then eluted with 8 CV of either 20 mM Tris, 60 mM acetate, pH 8.0±0.1 (bsAb C) or 20 mM Tris, 40 mM acetate, pH 8.0±0.1 (bsAb D). Pools were collected from $UV_{280nm}$ lift off to the end of the elution step. Following elution, columns were cleaned with 2 CV of 2 M NaCl followed by 2 CV of 1 M NaOH.

Host cell protein ("HCP") quantification was performed using a commercially available ELISA kit Cat # F550 (Cygnus Technologies). Soluble aggregate quantification by two ACQUITY UPLC PrST SEC Columns, 200 Å, 1.7 µm, 4.6 mm×150 mm cat #186005225 in series in a 10 mM sodium phosphate, 500 mM sodium chloride, pH 7.0 mobile phase. Bispecific purity was measured using three prepacked POROS A 20 µm columns (2.1 mm×30 mm, 0.1 mL) cat

2-1001-00 in series and an isocratic elution buffer system. Bispecific and FcFc titers were measured using a POROS A 20 µm column (2.1 mm×30 mm, 0.1 mL) cat #2-1001-00, and Fc*Fc* titers were measured by loading the flowthrough over a POROS G 20 µm column (2.1 mm×30 mm, 0.1 mL).

The invention claimed is:

1. A method of making a protein comprising:
   a. loading an affinity matrix with a mixture of multimeric proteins comprising (i) a first homodimer comprising two copies of a first polypeptide, and (ii) a heterodimer comprising the first polypeptide and a second polypeptide, wherein the first polypeptide has greater affinity for the affinity matrix than does the second polypeptide, wherein the affinity matrix comprises a Protein A ligand affixed to a substrate comprising a multiplicity of particles having a mean diameter of 45 µm and comprising pores having a mean diameter of 1100 Å; and
   b. eluting and collecting the heterodimer from the affinity matrix in a buffer comprising $CaCl_2$ or $MgCl_2$ and having a first pH range,
   wherein the first homodimer elutes from the affinity matrix in the buffer at a second pH range.

2. The method according to claim 1, wherein the mixture of multimeric proteins comprises a second homodimer comprising two copies of the second polypeptide.

3. The method according to claim 2, wherein the second homodimer elutes from the affinity matrix in the buffer at a third pH range, wherein the third pH range comprises a higher pH than the first pH range, which comprises a higher pH than the second pH range.

4. The method according to claim 1, wherein the substrate comprises any one or more of agarose, poly(styrene divinylbenzene), polymethacrylate, cellulose, controlled pore glass, and spherical silica.

5. The method according to claim 1, wherein 5 to 50 grams of protein is loaded per liter of affinity matrix.

6. The method according to claim 1 comprising the step of applying a pH gradient to the loaded affinity matrix of step (a).

7. The method according to claim 6 comprising the step of washing the loaded affinity matrix of step (a) with a solution at pH 6-8 prior applying the pH gradient.

8. The method according to claim 7, wherein the pH gradient is run between pH 6 and pH 3.

9. The method according to claim 1, wherein the first pH range is selected from a range within pH 5.5 and pH 3.6.

10. The method according to claim 9, wherein the buffer comprises acetate.

11. The method according to claim 10, wherein the buffer comprises 40 mM acetate.

12. The method according to claim 1, wherein the buffer comprises $CaCl_2$.

13. The method according to claim 12, wherein the buffer comprises 250-500 mM $CaCl_2$.

14. The method according to claim 1, wherein the buffer comprises $MgCl_2$.

15. The method according to claim 14, wherein the buffer comprises 250-500 mM $MgCl_2$.

16. The method according to claim 1, wherein the heterodimer comprises a bispecific antibody.

17. The method according to claim 16, wherein the first polypeptide comprises a CH3 domain that is capable of binding to Protein A and the second polypeptide comprises a CH3 domain that is not capable of binding to Protein A.

18. The method according to claim 17, wherein the second polypeptide comprises a HY to RF substitution in its CH3 domain.

19. The method according to claim 1, wherein the mixture of multimeric proteins is produced by a plurality of eukaryotic cells in a cell culture.

20. The method according to claim 19, wherein the eukaryotic cells comprise Chinese hamster ovary (CHO) cells or derivatives thereof.

21. The method according to claim 1 comprising the steps of:
   c. applying the collected heterodimer of step (b) to a multimodal chromatography resin in a buffer having an acidic pH;
   d. eluting the heterodimer from the multimodal chromatography resin in a buffer having a more alkaline pH; and
   e. collecting the heterodimer.

22. A method of producing a protein comprising the steps of:
   a. loading a first affinity matrix comprising a Protein A ligand affixed to a substrate with a mixture of multimeric proteins, the mixture comprising:
      i. a first homodimer comprising two copies of a first polypeptide,
      ii. a heterodimer comprising the first polypeptide and a second polypeptide, and
      iii. a second homodimer comprising two copies of the second polypeptide;
   b. washing the second homodimer from the first affinity matrix in a wash buffer;
   c. eluting and collecting the first homodimer and the heterodimer from the first affinity matrix;
   d. loading a second affinity matrix comprising a Protein A ligand affixed to a substrate with a mixture comprising the first homodimer and the heterodimer collected at step (c);
   e. eluting and collecting the heterodimer from the affinity matrix in a buffer having a first pH range and comprising $CaCl_2$ or $MgCl_2$,
   wherein, the first homodimer elutes from the affinity matrix in the buffer at a second pH range, and
   wherein the first affinity matrix, the second affinity matrix, or both comprise a Protein A ligand affixed to the substrate, wherein the substrate is a particle and the first affinity matrix, the second affinity matrix, or both comprise a multiplicity of particles of a mean diameter of 45 µm and comprising pores having a mean diameter of 1100 Å.

23. The method according to claim 22, wherein the substrate of the first affinity matrix, the second affinity matrix, or both comprise any one or more of agarose, poly(styrene divinylbenzene), polymethacrylate, controlled pore glass, and spherical silica agarose.

24. The method according to claim 22, wherein 5 to 50 grams of protein in the mixture of multimeric proteins is loaded onto the first affinity matrix.

25. The method according to claim 24, wherein 5 to 50 grams of protein in the mixture comprising the first homodimer and the heterodimer collected at step (c) is loaded per liter of second affinity matrix at step (d).

26. The method according to claim 22 comprising the step of applying a pH gradient to the loaded affinity matrix of step (d).

27. The method according to claim 26, wherein the pH gradient is run between pH 6 and pH 3.

28. The method according to claim 22, wherein the first pH range is between pH 5.5 and pH 3.6.

29. The method according to claim 22, wherein the buffer of step (e) comprises acetate.

30. The method according to claim 29, wherein the buffer comprises 40 mM acetate.

31. The method according to claim 22, wherein the buffer of step (e) comprises $CaCl_2$.

32. The method according to claim 31, wherein the buffer comprises 250-500 mM $CaCl_2$.

33. The method according to claim 22, wherein the buffer of step (e) comprises $MgCl_2$.

34. The method according to claim 33, wherein the buffer comprises 250-500 mM $MgCl_2$.

35. The method according to claim 22, wherein the heterodimer comprises a bispecific antibody.

36. The method according to claim 35, wherein the first polypeptide comprises a CH3 domain that is capable of binding to Protein A and the second polypeptide comprises a CH3 domain that is not capable of binding to Protein A.

37. The method according to claim 36, wherein the second polypeptide comprises a HY to RF substitution in its CH3 domain.

38. The method according to claim 22, wherein the mixture of multimeric proteins is produced by a plurality of eukaryotic cells in a cell culture.

39. The method according to claim 38, wherein the eukaryotic cells comprise Chinese hamster ovary (CHO) cells.

40. The method according to claim 22 comprising the steps of:
  f. applying the collected heterodimer of step (d) to a multimodal chromatography resin in a buffer having an acidic pH;
  g. eluting the heterodimer from the multimodal chromatography resin in a buffer having an alkaline pH; and
  h. collecting the heterodimer.

* * * * *

UNITED STATES PATENT AND TRADEMARK OFFICE
CERTIFICATE OF CORRECTION

| | |
|---|---|
| PATENT NO. | : 10,626,142 B2 |
| APPLICATION NO. | : 14/808171 |
| DATED | : April 21, 2020 |
| INVENTOR(S) | : Andrew Tustian et al. |

It is certified that error appears in the above-identified patent and that said Letters Patent is hereby corrected as shown below:

In the Claims

Claim 40
Column 22, Line 12:
"step (d)"
Should read:
--step (e)--

Signed and Sealed this
Twenty-ninth Day of November, 2022

Katherine Kelly Vidal
*Director of the United States Patent and Trademark Office*